(12) United States Patent
Budd et al.

(10) Patent No.: US 7,391,515 B2
(45) Date of Patent: Jun. 24, 2008

(54) AUTOMATED VISUAL INSPECTION SYSTEM FOR THE DETECTION OF MICROBIAL GROWTH IN SOLUTIONS

(76) Inventors: Gerald Walter Budd, 36853 Heatherton Dr., Farmington, MI (US) 48355; Julius Z. Knapp, 22 Foxwood Dr., Somerset, NJ (US) 08873

(*) Notice: Subject to any disclaimer, the term of this patent is extended or adjusted under 35 U.S.C. 154(b) by 358 days.

(21) Appl. No.: 11/244,749

(22) Filed: Oct. 5, 2005

(65) Prior Publication Data

US 2006/0072111 A1    Apr. 6, 2006

Related U.S. Application Data

(60) Provisional application No. 60/615,981, filed on Oct. 5, 2004.

(51) Int. Cl.
    *G01N 21/90*   (2006.01)
(52) U.S. Cl. ......................... 356/427; 356/335
(58) Field of Classification Search .............. 356/427, 356/335
    See application file for complete search history.

(56) References Cited

U.S. PATENT DOCUMENTS 3,914,058 A * 10/1975 Knapp et al. ................ 356/427

* cited by examiner

*Primary Examiner*—Roy M Punnoose

(57) ABSTRACT

Essential prerequisites for any injectable product are its sterility, its freedom from pathogens and its freedom from visible particle contamination . . . . These requirements must be satisfied prior to the release of an injectable product batch for sale and use.

A major difficulty in responding to these assay requirements is the need for a size sensitivity difference of 100 or greater in determining the presence of viable pathogenic organisms and of non-viable random particle contaminants. The wide dynamic testing range cannot be satisfied in current art with a single non-destructive testing station. The present invention uses a special agitation procedure to generate separate liquid volumes containing the small viable and larger non-viable particle contaminants. This separation makes possible the introduction of sensing systems that have been optimized for each size range and that can operate in parallel without interference.

12 Claims, 7 Drawing Sheets

Top View of Illumination Block
Thru Section A-A

Section B-B

AUTOMATED VISUAL INSPECTION SYSTEM FOR THE DETECTION OF MICROBIAL GROWTH IN SOLUTIONS

CROSS-REFERENCE TO RELATED APPLICATIONS

I claim priority to my Provisional Patent Application No. 60/615,981 with filing date Oct. 5, 2004.

DESCRIPTION

1. Field of the Invention

This invention relates to the procedures and devices utilized in the optical inspection of transparent containers for the presence of contaminating microbial growth in media fill, contaminating particulate matter and particularly to inspection of injectable pharmaceutical preparations.

2. Background of the Invention

The inspection for and elimination of visible particle contaminated containers from a batch of injectable pharmaceuticals is a United States Pharmacopeia requirement. This inspection is specified to be, whenever possible, after the product is in its final container. Evaluation that the visible particle incidence rate is within USP acceptance limits for human or veterinary use is an essential part of the injectable batch release procedure. It is also an essential prerequisite to the continuous improvement of the quality of an injectable product batch and to the reduction of product cost. These ends have been achieved by incorporating advances in behavioral science, physics and biophysics, illumination and mechanical engineering, pharmaceutics and statistics into a single analytical structure.

Any proposed inspection for visible contaminating particle size in an injectable product, manual semi-automated or fully automated must be validated before it can be used on a USP listed product. Validation in this GMP sense means that it must be demonstrated to be at least as effective as the preceding method or mechanism. The preceding method of inspecting injectable products for contaminating particles was the inspection of single containers by clinical staff at the injection site.

As shown by one of the authors in several papers, visible contaminating particles are randomly distributed throughout the batch. As such, a validated 100% inspection is essential to achieve accurate, sensitive contaminating particle incidence rate results. The use of the Attribute Sampling Inspection Tables with raw visible particle inspection data results in the incorrect rejection of good batches and incorrect acceptance of undesirable batches. The use of the Knapp-Abramson analysis framework provides the methodology, which transforms raw visible particle inspection data into a form acceptable to the Sampling Tables. For general use, the sensitivity and accuracy of the batch reject rate makes its use more desirable than decisions reached with the model based Sampling Inspection. Although the use of Attribute Sampling Assay Tables can be made compatible with raw visible inspection data, its limited sensitivity and the need to interpret the probability of the results obtained may very well shrink its future use to that of an investigators tool.

The authors of this inventions have been issued several patents in this field of study to aid the in the detection of particles in solutions. U.S. Pat. No. 6,498,645 describes a method for substantially complete detection of all particles, within a predetermined size range, contained in vessel containing an injectable solution. The method measures the blur fringe of particles as they move past the sensor in region near the inner wall of the container.

An improved technology was developed in 2003 the described a unique illumination and optical image system that increased the sensitivity of the detection system, currently the patent is pending (patent application Ser. No. 10/981,801, filed Nov. 5, 2004). The illumination technique and the detector-viewing angle allowed the inventors to examine the complete contents of the container being inspected. The technology allowed the system to identify heavy contaminating particles resting of the bottom of container, something that was not possible using previous technology.

A further improvement of the technology was disclosed in a more recent patent application (patent application Ser. No. 11/076,375, filed Mar. 9, 2005) in which the contributions of fluid dynamics in small vessels made it possible to precisely position contaminating particles within the container. This allowed the introduction of a visible particle standard set in which the dimensions of the progressively sized single particles are traceable to the primary dimensional standards maintained by NIST makes possible the generation of a calibration curve. This calibration curve relates particle size to particle detectability providing a stable, transportable, national and international reference standard of particle visibility. The conversion of the prime particle visibility parameter from detection probability to the measurement of particle size results in a measure better suited to continuous monitoring and quality adjustments in a production environment.

Combining NIST traceable sizing of stable microspheres with statistically accurate determinations of their rejection probability has made possible realization of a calibration curve relating the probability of manually detecting a contaminating particle to its NIST traceable maximum physical size. With USP acceptance and use of this calibration curve, inspection sensitivity and discrimination can both be defined and securely evaluated.

The ability to isolate contaminating particles with accurate sizing and repeatability lead to the discovery that microbial growth could to monitored over a period of time. The previous patent application (Ser. No. 11/076,375 and its provisional patent application counterpart) for the optimized motion profile to control the fluid dynamics in small containers provided a method to position contaminating particles so that they could be measured. The present invention takes the technology one step further in that it allows for the separation of different density materials along the axis of rotation. Thus microbial growth (biological materials) can be separated from contaminating particles (inorganic materials and man-made compounds) and monitored over a period of time.

BRIEF SUMMARY OF THE INVENTION

A study of the movement of liquid in sealed cylindrical containers, following the transfer of energy to the container, resulted in the conclusion that the observed movement of the liquid in the container was best described as non-linear in nature. In response to the energy transfer preferably by a defined sequence of acceleration, constant velocity and deceleration a toroidal liquid flow in the sealed container was generated. The toroidal flow, when optimized, was laminar in appearance. The flow pattern was down at the walls across the bottom, up on the spin axis and across the meniscus to complete the flow pattern.

Adjustment of the spin parameters results in a size separation of the particles in the container into three defined volumes: near field, axial flow and far field. The upward flow pattern at the center of the container, the spin axis, makes possible a designed segregation of any particles present in the container into sub-visual sizes on the spin axis and detection of visible particles in the near and far field particle volumes. The fact that particle size segregation has been imposed on the contents of the container makes possible a simultaneous coordinated size range defined design separately optimized for the optical and electronic required in the visible and sub-visible particle sizes.

The present economically effective availability of single container identification using for instance 2-D bar coding and high speed mass memory in combination with the new sizing and sorting capability described here makes possible:

1) High sensitivity sterility testing in a fraction of the 14 days presently required.
2) Adjustment of the pattern of heat flow in the sterilization autoclave to increase the duration accuracy of the sterilization cycle and thus the accuracy of the sterilization throughout all the containers in the batch.
3) The combination of the capability to determine the distribution of particle sizes in individual sealed containers provides an essential new tool with which to examine the effect of formulation changes and the stability of new injectable products.

The combination of the sizing and sorting of identified sealed containers makes possible the combination of the U.S. Pharmacopeia required sterility testing of the manufacturing process with a determination of the base reject rate of the functioning parenteral process. This additional capability increases in importance as the cost of the pharmaceutical product continues to increase.

At the present time, quality testing on pharmaceuticals is focused solely on the quality of individual components. This can be compared to the testing of the individual components of an engine neglecting the dynamic testing of assembled engine performance. The result of this component testing philosophy is that manufactured product is used to make the final process adjustments. This philosophy was acceptable in the manufacture of antibiotics but is less acceptable as product cost increases.

The capability of a combination test using the required full scale media fill test of sterility and combining it with a determination of the randomly sourced visible particle contamination that will be encountered is seen as a way to increase quality and simultaneously reduce production costs.

It is an object of the present invention to transform the present probabilistic detection of contaminating particles and microbial growth present in a container, even larger than 30 mm in diameter, into a deterministic detection and accurate measurement process.

It is a further object of the present invention to provide a method to position the contaminating particles and microbial growth in an injectable solution into a well-defined volume in the container to enhance the detection and measurement of contaminating particle(s) and/or the microbial growth.

It is a further object of the present invention to provide a method to define the mechanical requirements to produce the capability of positioning the contaminating particles and/or microbial growth in the defined inspection volume of the fluid fill.

It is a further object of the present invention to define a "Velocity Motion Profile" that will optimize the fluid dynamics of the system so to reproduce the position of the contaminating particles and/or microbial growth in the inspection volume.

It is a further object of the present invention to define the a unique "Velocity Motion Profile" for each inspection system based on the size and shape of containing vessel, the amount of fluid fill in the container and the viscosity of the media fill fluid containing the contaminating particle(s) and/or the microbial growth.

It is a still further object of the present invention to provide a method to separate the various density contaminating particles and microbial growth in the media fill into specific regions in the container.

It is another object of the present invention to provide a method for recording the apparent size of the contaminating particles so that they can be tracked over a period of time. The system includes the necessary mechanical and electrical hardware, software, and velocity motion profile and physical characteristics of the product being inspected.

Generally the present invention provides an improved method for the detection and measurement of all particles and microbial growth, within a predetermined size and density range, contained in a media fill solution, in a transparent container.

A short description of the mechanical and optical equipment used in the inspection device is provided here. A more detailed description and drawing of the apparatus is contained in U.S. patent application Ser. No. 10/981,801 filed on Nov. 5, 2004 and Ser. No. 11/076,375 filed on Mar. 9, 2005. The '801 patent applications' primary concern is that of the physical devices used to illuminate and acquire images of the particles. The '375 patent applications describes a method to position the particle in the container for a more accurate measurement of size.

The method comprises the steps of:
a) pre-positioning particles in the container whereby rotation of the container causes substantially all of the particles in the injectable solution in the container to rotate, with approximately equal initial velocity, in a shell volume adjacent the inner walls of the container, with said shell volume having a predetermined thickness;
b) as more energy is imparted in the velocity motion profile the fluid will experience a toroidal motion in which fluid will move along the container bottom toward the center of axis of rotation, upward along the axis of rotation and then downward along the container walls;
c) the proper velocity motion profile will cause the migration of particle from the inner wall of the container toward the center of the container;
d) the degree of migration of the particle is directly related to the mass of the particle, heavy particles will migrate only slightly away from the wall, particles with less mass will migrate toward the bottom center of the container, and particles with the least mass will be moved to the center of the container and lifted from the floor of the container;
e) the lower density contamination (microbial growth) will be concentrated about the axis of rotation and above the floor of the container;
f) it is desirable to use a velocity motion profile that will position particles in the mass range being studied in a small volume on the bottom of the container at the center of rotation, referred to as the optimized inspection volume (OPTIV);
g) illuminating all the particles within the optimized inspection volume with lighting means;
h) detection of particles by movement on the container bottom and in solution by orienting the sensor with a downward angle with respect to the axis of symmetry of the container;
i) detecting at least one of light scatter, light reflection and light extinguishing caused by said particles, with detector means having a depth of focus of detection in which said particles remain in near-focus within the optimized inspection volume of the container;

j) detection and measurement of the microbial growth (biological material) will be primarily by light extinction as the opacity of the solution is reduced as the microbial growth contamination becomes more prevalent; and k) measuring at least one of light scatter, light reflection and light extinction caused by said particles, with detector means having a depth of focus of detection in which said particles remain in focus within the optimized inspection volume of the container.

wherein the sensed signal is corrected for the asymmetries of the imaging system by correction means either by computation or by repositioning the detector means relative to the container, whereby a focused imaging plane is formed at the container axis and then mechanically or electro-mechanically offset closer to the imaging sensor than the center of the cross section, whereby the size of detected particles in the opposite volumes is accurately mathematically compensatible to an actual size. The lighting means provides a multiplicity of directed light emitting diodes (LED's), mounted on three of the interior walls of a cubic structure with an acrylic "U" shaped diffusing element and the container under inspection placed in the center.

With said detector being mounted inside a sealed enclosure the critical optical components of the system can be protected from the environment. The detector is mounted in such a manner so that so that the optical path can be easily adjusted with the target area. The design of the sensor enclosure allows for the insertion of optical filter elements within the optical path of the invention.

Contaminating materials with less optical density can be enhanced in the image by reducing the radiant energy of the illumination system. The illumination system provides a means of stable uniform light that can be used for an opacity measurement of the solution. A clear solution will attenuate the light less than that of a torpid solution. In the case of media fill samples the opacity of the solution can be monitored over a period of time and small changes in the opacity can be measured and recorded. Over time a baseline for a specific product will be established and any deviation from the nominal opacity can be measured. The media fill samples will be labeled with a unique identification via 2-D bar code or human readable code that can be read electronically. The media fill samples can then be tracked (electronically) at the time of each inspection and any change in the contents can be measured and recorded.

These and other objects, features and advantages of the present invention will become more evident from the following discussion and drawings in which:

DETAILED DESCRIPTION OF THE INVENTION

The invention is a combination of mechanical, electronic, and software components configured in the proper way to produce information that will yield repeatable measurement results.

The basic components of this invention have been described in detail in U.S. patent application "An NIST Traceable Automated Inspection System for an inspection of particles in solution" (Ser. No. 10/981,801 filed on Nov. 5, 2004) and U.S. patent application "Small container fluid dynamics to produce optimized inspection conditions" (Ser. No. 11/076,375 filed on Mar. 9, 2005). The components used are essentially the same except that the software and optimized motion profile (spin conditions) have been modified to extract information relative to the detection of microbial growth in media solutions. The figures are provided here to illustrate relative position of key components used in the present invention.

Figure 1:
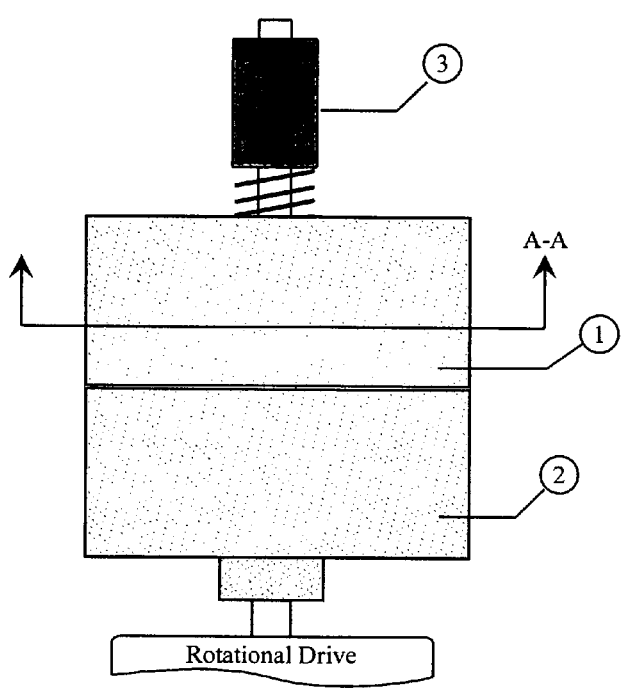
FIG. 1—Side View of Illumination Module resting above the rotational device.

The first key component is a unique illumination system designed to provide a very uniform background for the inspection of product in cylindrical vessels such as pharmaceutical vials. The illumination system is cube shaped with a channel slightly larger than the diameter of the vessel removed from the center, hereafter we shall reference to this system as the illumination module. The basic configuration is illustrated in FIG. 1. The cube is constructed using an upper and lower halves indicated by items 1 & 2. The construction is from a solid piece of aluminum that has material removed to hollow its inner. The aluminum is anodized black to insure that no reactive surfaces are on the components. The sample product (pharmaceutical vial with liquid contents) is centered on a recessed puck and held in position by a spring loaded clamping device. Item 3 in the illustration represents the retaining sleeve for spring and alignment shaft.

Figure 2:
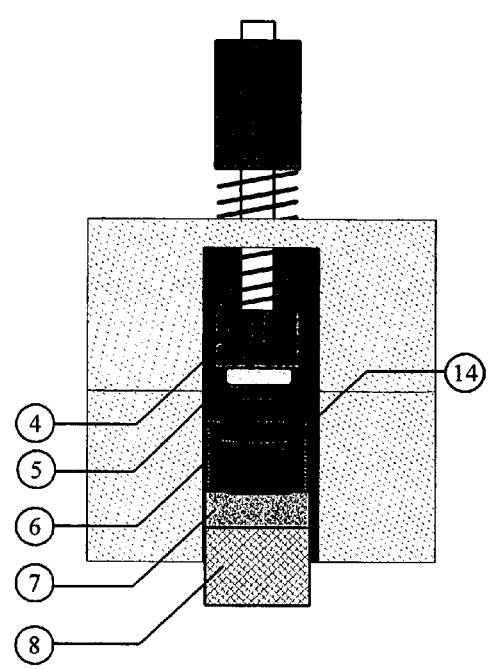
FIG. 2—Front View of Illumination Module with a small vial (container) resting in the inspection position.

FIG. 2 illustrates the front view of the illumination cube with the channel exposed. The sample product (item 14) is positioned on a recessed bottom holder (item 7). The cap of the sample product (item 5) is usually constructed of a rubber liner (cap) and a protective aluminum closure. The clamping device use to securely hold the sample container during rotation also has a recessed cup in the contact area to center the sample (item 4). The clamping device incorporates ball bearings to insure that the closure on the sample is not damaged.

The recessed bottom holder has two different recessed diameters on the top and bottom surfaces. The recessed holder is held tightly during rotation of the drive mechanism (item 8 and rotational drive of FIG. 1) using three equally spaced pins. The inspection window (item 6) is centered in the most uniform area of the illumination field. The illumination field is made uniform by properly shaping the diffusing media and adjusting the LED lighting sources.

Figure 3:
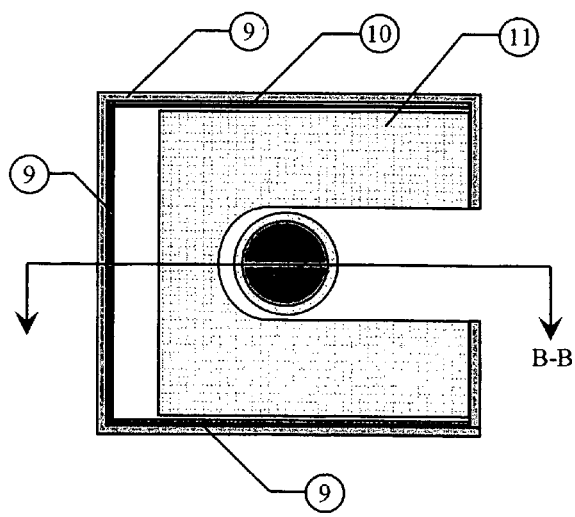
FIG. 3—Top View of Illumination Module through Section A-A illustrating the position of test container relative to the illumination module.

FIG. 3 is the top view of the illumination module as seen through section A-A of FIG. 1. The Aluminum housing (item 9) is hollowed out to leave only a thin wall. Placed around the three walls opposite the opening, are flat panels light emitting devices (LED's). The LED flat panels are fabricated with a high density of LED's per unit area; reference Phoenix Imaging 4100 series LED backlights. The LED panels provide a uniform illumination and can be turned on or off as required for the inspection. The uniform illumination field is created using a special design diffusing media, item 11 in FIG. 3. The diffusing media is fabricated from a cube of optical grade polycarbonate or acrylic. As can be seen in the Figure the test sample is placed along the centerline of the illumination module. A cutout shaped like an elongated "U" is made in one side and faces the optical sensor. The cutout is slightly larger than the diameter of recessed bottom holder and test sample. The LED illumination panels can be adjusted for backlight, diffuse sidelight (forward scatter) or a combination of both. A voltage controller allows the output of the LED lighting panels to set for optimum contrast/performance. The front surface of the illumination module, except for the viewing channel, is hidden by the aluminum housing to protect over exposure of the sensor from the LED lighting panels.

Figure 4:
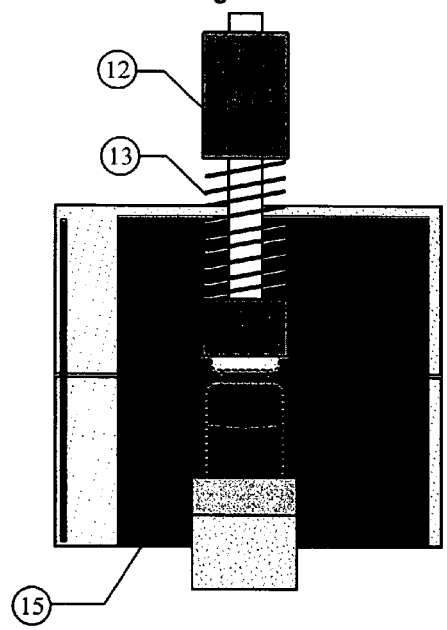
FIG. 4—Side View of Illumination Module through Section B-B illustrates the position of LED panels in the illumination module.

FIG. 4 illustrates the cut away view of the illumination module as seen through section B-B of FIG. 3. The illumination diffuser and LED panels extend below the bottom of the sample vessel to insure uniform lighting across the entire image. This unique design hides the corners of the LED panels and makes the entire illumination field a uniform intensity. Variations in the height of sample container are accommodated in the inspection position with the aid of compliance spring (Item 13) and low friction guide (item 12). Unlike previous designs this system allows particles in the solution to be tracked throughout the entire volume. The technology implements high-resolution area scan sensors that acquire full frame images in several milliseconds. The sensor is able to scan the entire volume of the solution each frame. The detection of particles >40 μm are isolated with 100% certainty within the inspection cycle.

Figures 5, 6, 7:
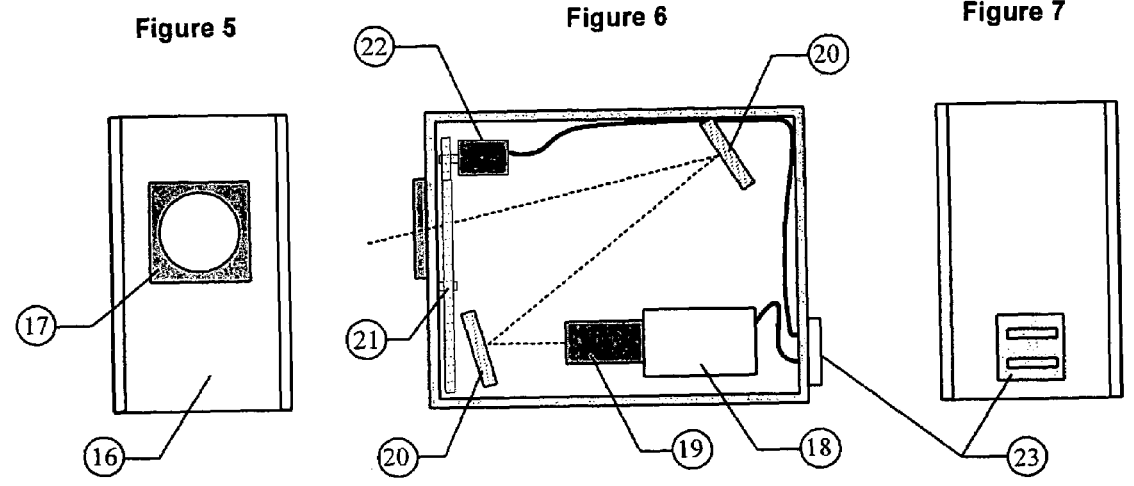
FIG. 5—Front View of Sensor Module with exit window.
FIG. 6—Side Profile View of Sensor Module illustrating the position of key optical components in the sensor module.
FIG. 7—Rear View of Sensor Module illustrating electrical connection ports.

The second major component in the inspection system is the Sensor Module. The sensor module is designed as sealed unit with no user serviceable components. The image sensor, optics, filters are pre-calibrated in known positions in the sensor module. FIG. 5 illustrates the front surface of the sensor module (item 16) and the viewing window (item 17). The viewing window is constructed using a material with anti-reflective coating. The window is sized to accommodate the field of view (FOV) necessary to acquire the image of the sample under inspection.

FIG. 6 illustrates one internal configuration of the Sensor Module. The photosensitive detection system used in the sensor module is either a high-resolution CCD sensor or in some applications a sensitive CMOS sensor may be used. The CCD sensor (item 18) must be of mega-pixel resolution or larger and is located in one corner of the sensor module. The optical system is very important in the detection of small particle in solutions. High quality lenses should be used to enhance performance of the inspection (item 19). The optical path length (the distance between the CCD sensor and the sample under inspection) has an effluence of the imaging characteristic and performance of the system. In some cases the path length must be longer than the available distance between the physical location of the CCD sensor and the sample under inspection. In this case, a folded optical path is employed by reflecting an image of the object through one or more mirror to increase the apparent distance between object and CCD sensor as illustrated by items 20 in FIG. 6. The longer the focal length of the lens, the greater the depth of field and therefore the larger volume that can be inspected. When instrument volume is at a premium the folded optical path allows for better system performance in a small footprint enclosure.

The sensor module incorporates an internal optical filter wheel. The wheel is a disk with one or more filters (grayscale attenuation or color) that allow the system to change the CCD sensor characteristics very rapidly. The filter wheel is illustrated as item 21 in FIG. 6. The filter wheel is optional and is not required for every inspection. The filter wheel is driven by a small stepper or servomotor (item 22) from inside the sensor module. The filter wheel may be substituted with a liquid crystal window in grayscale applications and has the benefit of not having mechanical moving components. The liquid crystal window attenuates the amount of light allowed to pass in the optical path. This ability to attenuate the optical path, whether electronically or mechanically is critical in the inspection application. The inspection process will be discussed later in this document.

Figure 8:
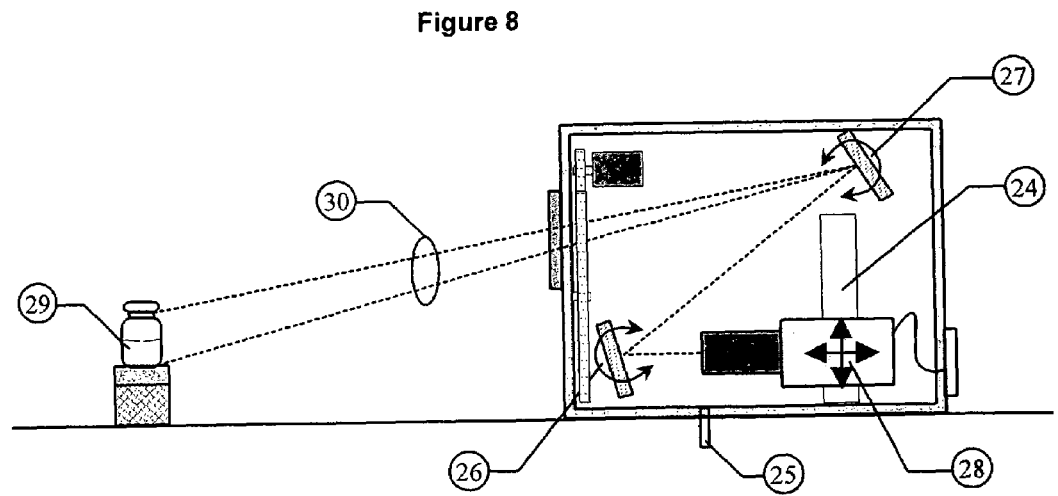
FIG. 8—Profile View of Inspection System Setup illustrating the sensors field of view.

The sensor module is a seal box with all optical devices mounted inside. The sensor connections are made by way of a multi-pin connector on the rear of the module. The multi-pin connector system allows the user to easily replace a defective sensor module with another sensor module that is pre-configured for the application with no user setup required. When the initial application is installed it defines the configuration of the sensor module. This configuration is archived at the plant of manufacture so that an exact duplicate sensor module can be assembled for use as required. On the bottom of the sensor module is a pair of holes designed to accept mating tapered dowel pins (item 25 of FIG. 8). The dowel pins only allow the sensor module to be installed in a specific location in the inspection system. The multi-pin connector is used to connect the sensor and aperture control (liquid crystal window or filter wheel) inside the sensor module without having the user open the enclosure.

The relative position of components with respect to each other is critical for system operation. The locations are defined by each application. Enhancements have been made to the interior of the sensor module to allow each unique configuration to be setup easily and quickly. The CCD sensor is mounted on one or more dovetails slides the permit the unit to translated in orthogonal directions as indicated by item 28 in FIG. 8. The dowel pins insure that the sensor module is mounted the proper distance from the object under inspection (item 29). The front surface mirrors used to guide the optical path use goniometer mountings for fine alignment of the field of view to the target position (items 26 & 27). The region of interest (ROI) when inspecting solution filled pharmaceutical vials is from the bottom of the meniscus to the bottom of the vial, as illustrated by item 29. The solid angle of the optical path defines the FOV of the image and is determined primarily by the focal length of lens used, identified as item 30. The solid angle of the optical path must be clear of obstructions.

Figure 9:
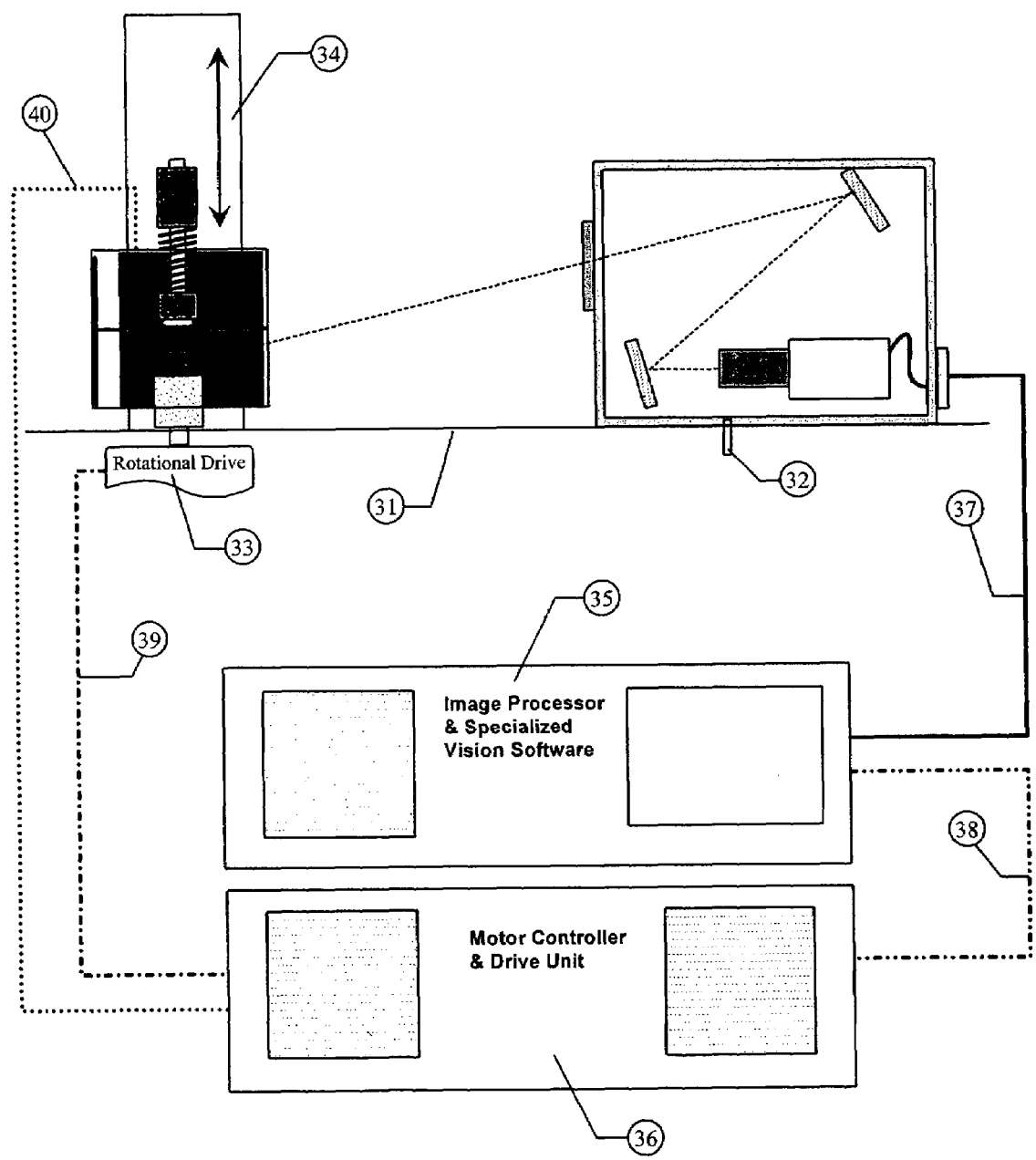
FIG. 9—Schematic of Inspection System with all major components.

FIG. 9 illustrates the complete configuration of a single inspection cell. The key components Illumination and Sensor Modules are mounted on a flat tabletop or work piece. The working distance and angle of viewing of the inspection cell is defined by the distance between the axis of rotation of the rotational drive (item 33) and the dowel pins (item 32). The object height above the work plane (item 31) is defined by the height of the recessed container holder mounted on top of the drive shaft. A word should be said about the rotational drive (item 33). The method of rotation is not as important as the parameters used to perform the function. The best results are achieved with a drive system that is capable of accelerating and decelerating quickly. The physics of the inspection require that the drive system accelerate rapidly, maintain a keep velocity and the then decelerate rapidly. The profile of the motion curve is very important and defines the motion or path of the contaminating particle in the solution. The wall of the vessel must couple with the solution within. It is important the acceleration/velocity profile does not cause cavitation (the generation of air bubbles in the solution). If cavitation is the result of the motion profile the sample can not be inspected. The motion profile must move the heavier particles without allowing the meniscus to creep up the walls to the vial neck. If the vial is spun to vigorously the particle may be spun up into the cap of the container and be held there. The correct motion profile of an inspection is defined by the size/shape of the container and the viscosity of the solution inside it. This inspection system allows the user to study the shape characteristics of the meniscus while defining the motion profile.

The Illumination Module is mounted on a linear translator that allows it to be raised and lowered. By raising the Illumination Module it provides clear access to the sample container and rotational drive/recessed holder. The linear translator (item 34) is normally positioned at the rear of the Illumination Module. This has the additional benefit of reducing the spacing between adjacent inspection units if more than one is implemented. The linear translator implementation can be assisted by air (cylinders), electric (or magnetic), or mechanical (lead screws or cams). The linear translator should be parallel to axis of rotation.

The third key component in the inspection system is the Image Processor and Specialized Vision Software. The Sensor Module sends image data (optical picture in electronic format) to the Image Processor (item 35). The image processor acquires high resolution (minimum 1280×1024 pixels) with a minimum signal to noise of 10 bits (1024 grayscale levels). Much higher resolution sensors may be used when cost or cycle times at not a critical. The preferred data transport mechanism is to use the Camera-Link (CL) format indicated as item 37. The analysis of the image data is performed using special software written to extract the particles in solution. The system acquires multiple HR images in rapid secession (4-60 images) and stores them in separate frame buffers. The sensor acquisition control allows the application to define the region of interest (ROI) from within the field of view (FOV). The system should use frame rates (number of full pictures per second) in the range of 24-60 frames per second. If partial frames are used to acquire images with smaller field of view the frame rates increase. The optimum frame rate is one in which the largest diameter particle (assuming spherical object) translates or moves at least one diameter between successive images. It may be the case that the viscosity or fluid motion is slow and a delay must be placed between successive image acquisitions. The software compares each image the previous image (except in the case of the first) and isolates any object with the image field of view that moves. A special image processing algorithm is used to extract the moving particles and then determine their relative size. The Image Processor (item 35) acts as the inspection cell master controller and controls the other modules or devices in the inspection cell.

The forth major component in the invention is the Motion Profile created with a motor, drive unit and controller. The Motor Controller (item 36) is used to generate the motion profile in conjunction with the rotation drive. The request to perform a motion profile is given to the motor controller over item 38. The control line between the motor controller and the motor is indicated by item 39. In the evaluation unit a high torque stepper motor with lower inertia was used to rotate the test sample. The motor controller also controlled turning the various LED lighting panels on or off during the inspection (item 40). When the motion profile has been completed the motor controller reports back to the image processor and the image processor will begin acquiring the necessary images. Depending on the number and size of image acquired the entire inspection cycle requires from one to several seconds.

Figure 10:
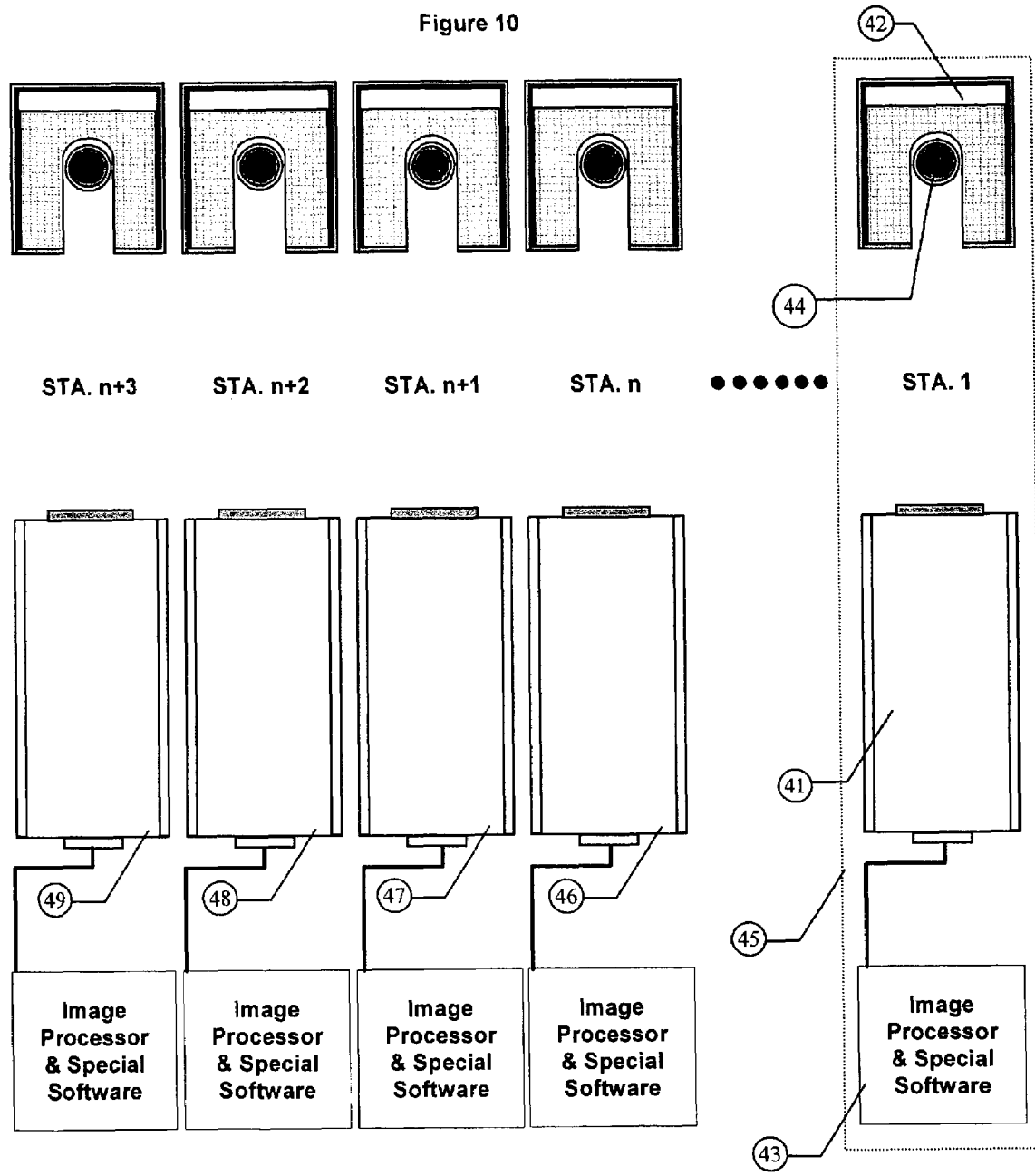
FIG. 10—Schematic of Multiple Inspection cell configuration.

If the average cycle time is three seconds for a rigorous inspection then the inspection cell is limited to 20 inspections per minute. The Laboratory Assay System is a small single inspection cell unit designed to handle a limited number of samples per hour. This does not lend itself toward mass production inspection. However, the design concept can easily be expanded to incorporate multiple copies of the inspection cell. FIG. 10 illustrate an approach that can handle the desired volume by implementing multiple inspection cells side by side. The inspection cell is indicated as item 45 and is comprised of a Sensor Module (item 41), an Illumination Module (item 42), an Image Processing Module (item 43) and the sample on rotational drive (item 44).

The large volumes of sample product would be moved into the inspection position; this may be performed at all stations simultaneously if desired. However simultaneous operation is not necessary as each inspection cell is independent. The simultaneous operation would reduce the cost of the rotational motion by using a common drive mechanism.

It would be difficult to hand-load the laboratory assay system at 20 vials per minute. However, if 10 stations were used in a large volume production system it would be easy to achieve 200 samples per minute. The key feature of this inspection technology is the ability to determine the size of particle inspection with an accuracy range of 20 µm with examining a 2-10 ml sample. The user can select an exact cut-off limit below which particles smaller than the limit will be accepted. The product is not rejecting simply on a detection basis but on a particle size basis.

When calibrated using NIST traceable standard samples the inspection system provides a method for validation for maximum dimensional particle sizing. This also provides a more realistic measurement of non-spherical particles like platelets, fibers and non-uniform shapes (glass shards). The Module concept provides NIST traceable inspection not only when shipped but virtually forever. This is possible because of a stable detector with permanent size calibration.

Figure 11:
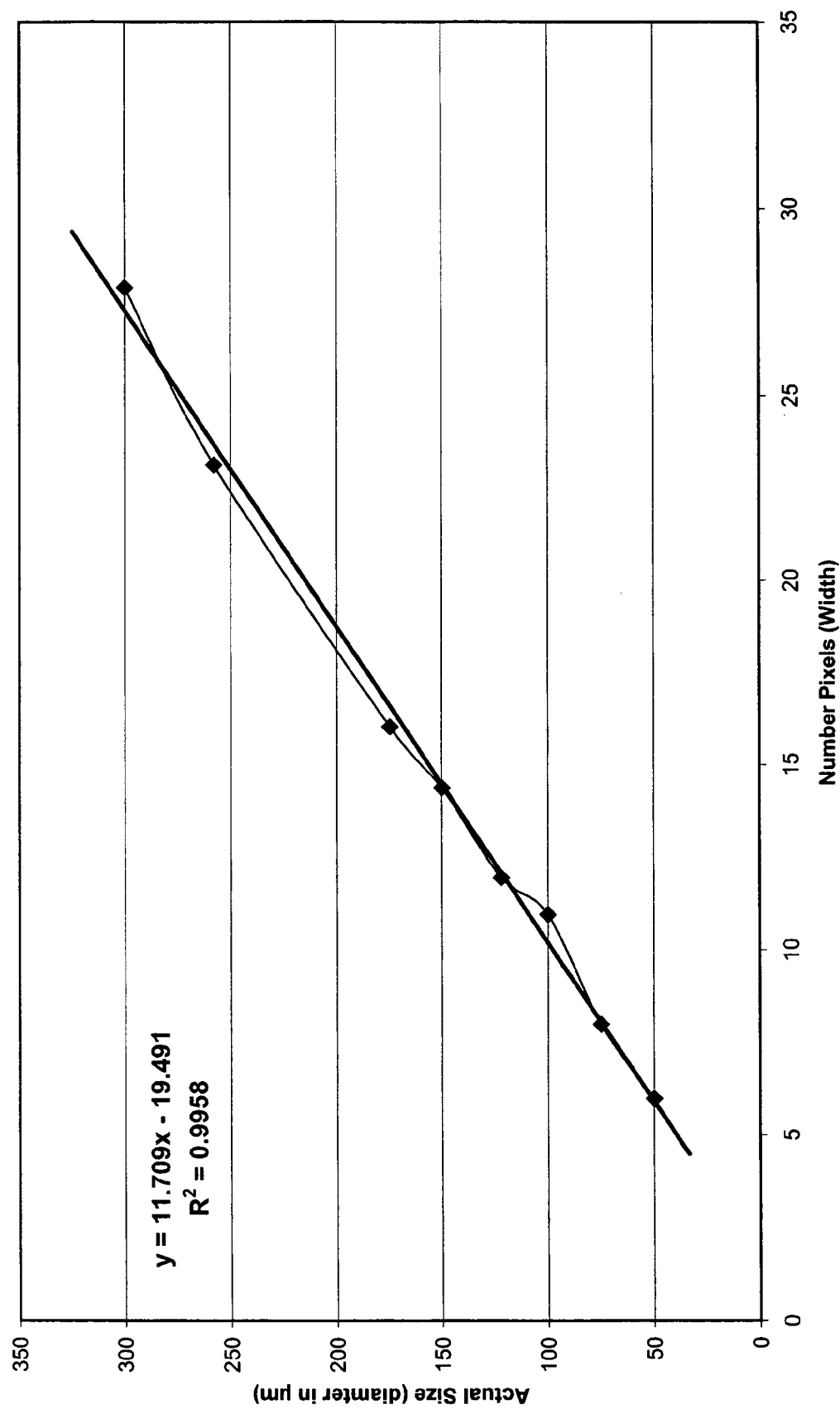
FIG. 11—Plot of Particle Size vs. pixel Count (Calibration Curve Small Particles) illustrates the resulting calibration curve for small particles (diameter <350 μm) using the velocity motion profile for WFI (Water for Injection)
Figure 12:
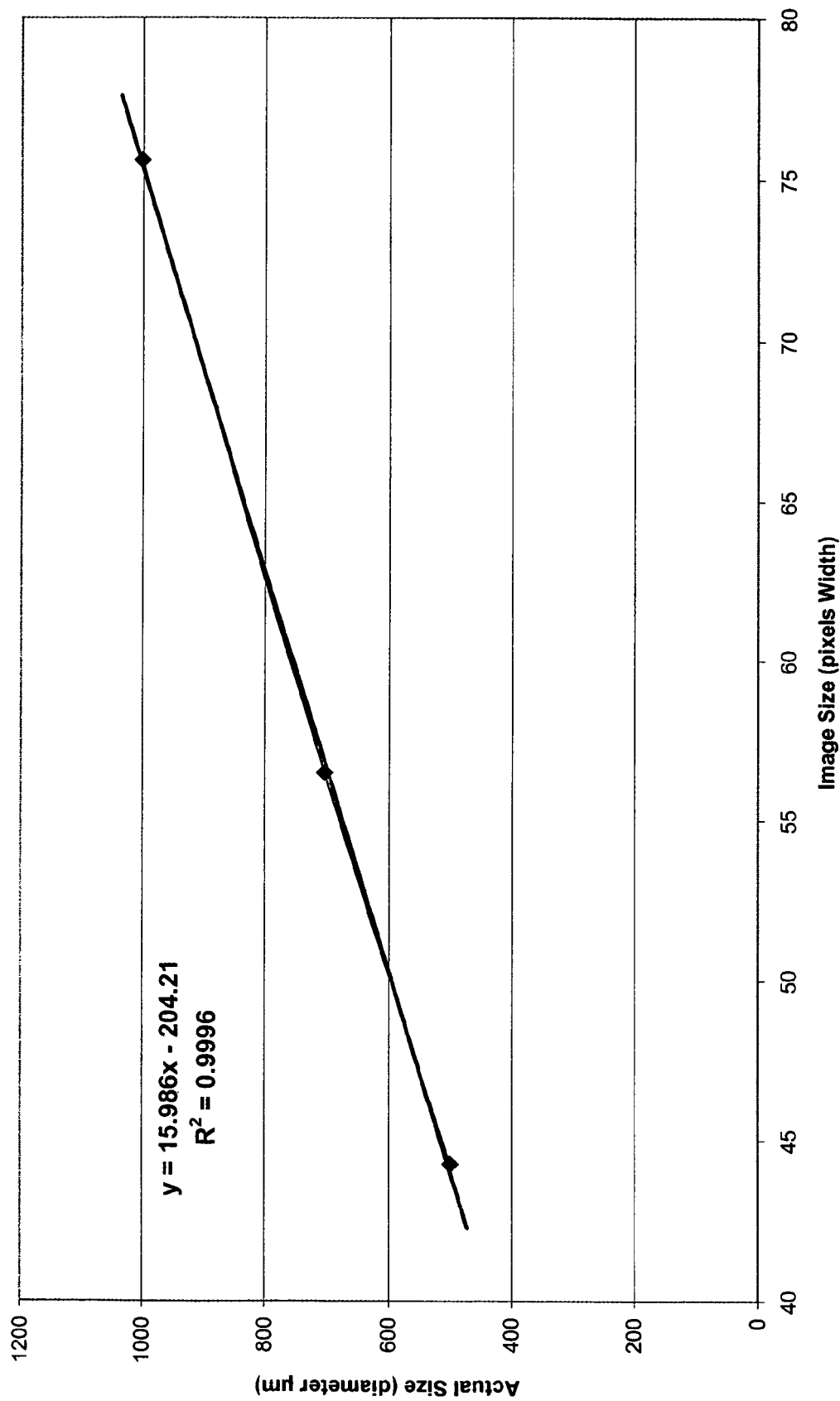
FIG. 12—Plot of Particle Size vs. pixel Count (Calibration Curve Large Particles) illustrates the resulting calibration curve for large particles (diameter >500 μm) using the velocity motion profile for WFI.

The ability to generate a linear calibration curve corresponding to each inspection volume is critical to the successful operation of this invention. FIG. 11 show the calibration curve central inspection volume using the WFI velocity motion profile. The curve was generated using a standard calibration set constructed using NIST traceable stainless steel spheres with a diameter range from 40 µm to 300 µm. The calibration curve is linear with an $R^2$ valve of >0.995. This calibration curve allows the present invention to determine the diameter of a particle in the center inspection volume to ±10 µm. The present invention can perform simultaneous independent evaluation of near-field and far-field images. The ability to size particles in the inspection volume to that accuracy provides a method that makes NIST traceable maximum particle size measurements possible with the generation of a calibration curve relating the probability of detecting a particle to its physical size. When this calibration curve is determined with microspheres that have been inspected under standard conditions (light quality and intensity, manipulation of the container, duration of the inspection, the background employed) and sized with NIST traceability, the basis for an accurate international standard of particle contamination quality has been established.

The standard (particle size)/(particle rejection probability) calibration curve can be considered an equivalent to the use of the set of standard microspheres used to calibrate particle counters. The probability that similar microspheres will be found in a biological or chemical suspension is small. The microspheres in the calibration sample are used to determine that the functionality of the visible particle inspection method or system has the sizing accuracy desired.

The U.S.P. designates the effectiveness of the manual inspection, which is available up to the moment of clinical use, as the benchmark inspection performance required. Any alternative inspection must be shown to be as effective as the benchmark manual inspection before it can be used on a U.S.P. listed product.

Figure 13:
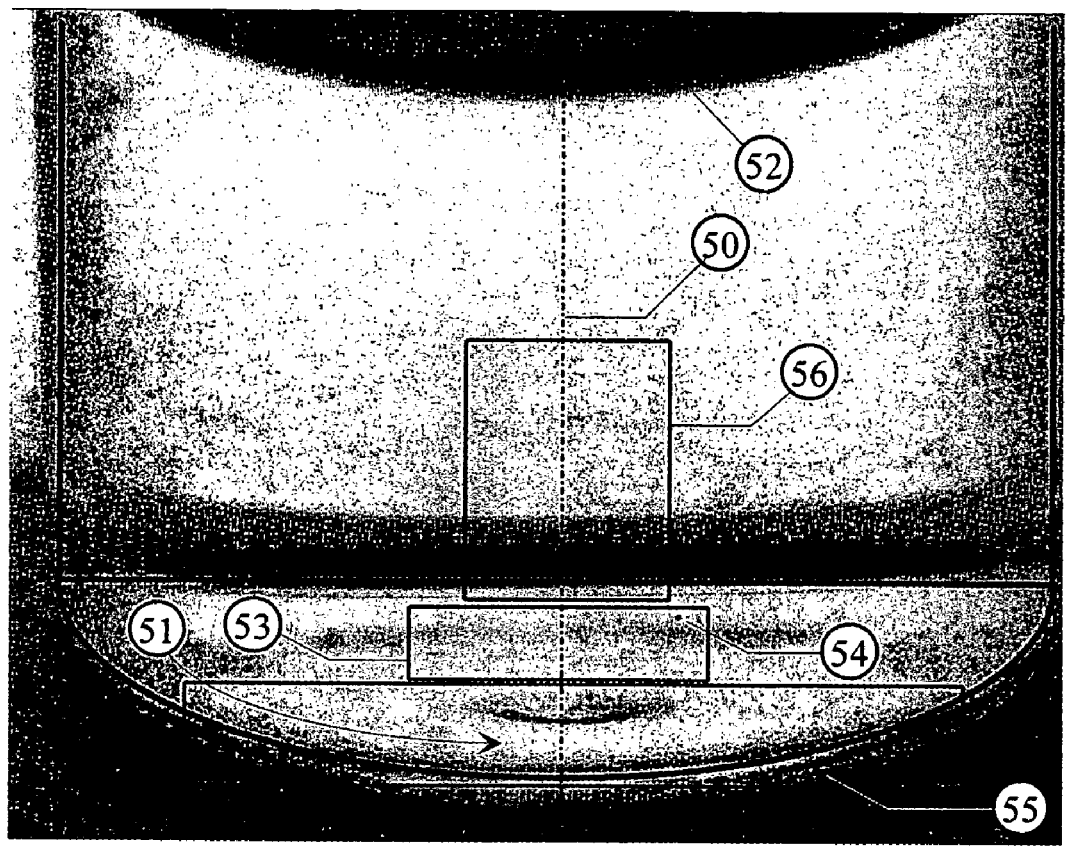
FIG. 13—Illustration of multiple inspection windows within a large field of view of one sensor that is used to view a large percentage of the fluid contents within the container.

FIG. 13 illustrates the position of multiple inspection windows within the larger field of view of the sensor used to view the major portion of the container. Item 50 is the central axis of rotation, the container is spun about this axis. As the container rotates the fluid with the container begins to move in the direction of rotation as indicated by item 51. The fluid/container wall interaction transfers energy to the fluid. As the container reaches higher rotational velocity the fluid begins to setup a vortex which pulls the fluid and its contents toward the center of the container. This vortex resembles a miniature tornado pulling the fluid and its contents upward along the center axis of rotation. The profile of the motion, acceleration, velocity and deceleration is critical and must be controlled as to not cause cavitation of the fluid and introduce air bubbles. The meniscus indicated by Item 52 should remain smooth for optimum results.

The particle under investigation is moved into a well defined region were it can be measured precisely. The particle is indicated by Item 54 in FIG. 13. The particle appears in the region on the bottom center of the container labeled Item 53. The particle less than 350 µm in diameter with a density equal to or less than 8.2 gm/cc will always appear in this region after the spin cycle is complete. The system will not impart enough energy into larger particles and they will simply move about the circumference of the inner diameter and appear in the zone indicated by Item 55. The particles that have a density greater than that of the fluid but less than about 1.8 gm/cc will be pulled upward by the vortex and appear in a region center on the spin axis and above the bottom of the container indicated by Item 56.

Figure 14:
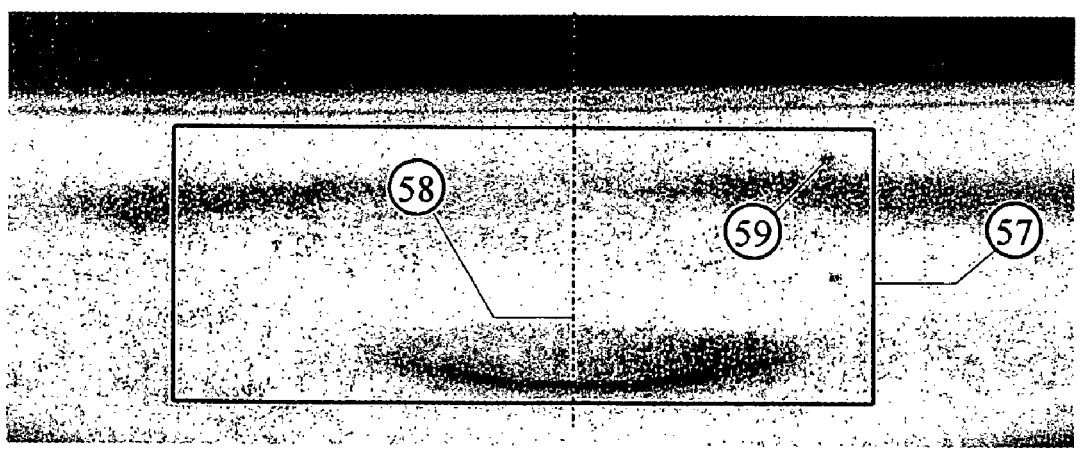
FIG. 14—Higher resolution image obtained from second sensor utilizing a smaller field of view to measure the contaminating particle size more precisely.

The second (additional) sensor has a higher magnification than the primary sensor and is centered about the axis of rotation, Item 58. The field of view of this sensor is illustrated in FIG. 14 and shows a much larger particle positioned in the inspection volume indicated by Item 57. The particle is indicated by Item 59 and can be measured more precisely because of the high sensor resolution.

The present invention improves the pixel resolution and speed of the sensors to improve the spatial resolving power of the invention from the previous generation device. The sensors resolution can be increase to 2,000×2,000 pixels with an acquisition rate of greater than 20 frames per second.

The present invention provides for one or more additional sensors to be implemented in the sensor module. The additional sensors can have a different magnification factors than the first sensor allowing for a different viewing angle or a smaller field of view and therefore higher resolution in a specific inspection volume. All sensors acquire the images simultaneously providing a more secure inspection and analysis. This greater sensitivity provides a measurement that is at least an order of magnitude greater that is capable with human inspection.

Another important feature of the present invention is the use of 2-D bar coding for the traceability of samples in the inspection process. The 2-D codes can be printed on the closure (aluminum or plastic) using either inkjet print or laser marker. This method of marking will require that the specimen be rotated in order to be read. This is possible in the inspection position since the container will be rotated for inspection. As an alternative method, a special adhesive label can be placed on the bottom of the container and read during the load/unload process.

By reading the sample identification during the inspection process results can be compared to previous inspection results. This methodology provides a means to determine the presence and/or rate of growth of contaminating biological material in media fill containers and tissue cultures.

The traceability data can also be used to determine the stability of the inspection equipment over time. If know standard sample sets are tested in the invention several times over a period of time out of control or non-linear components can be identified.

The traceability of sample positions inside an autoclave tray and the position of the tray in the stack can be used to determine whether a sample received the proper treatment in the autoclave. The ultimate temperature and length of time at temperature that a sample experiences while inside of an autoclave has a direct bearing on the quality of that sample.

The invention as described provides a method to combine the media fill test (biological contamination) and baseline particle contamination (non-biological contamination) testing simultaneously. The ability to perform this combination simultaneous is an important aid to the engineer for process validation.

The improvement described in the present invention applies to both the benchmark manual inspection as well as to semi- and fully automated contaminating particles inspection methods and mechanisms described herein.

What is claimed is:

1. A method and apparatus for increased sensitivity of one or more image sensors which permits the detection and measurement of changes in the solution opacity and/or particle size distribution over a period of time, within a predetermined size range, contained in an injectable solution, with a density greater than or less than the solution, in a transparent container therefore, said method comprising the steps of:
  a) Pre-storing the container at an angle to the vertical for a sufficient time to permit the movement of all particles to reach their stable positions in either the heel of the container or the high point of the meniscus;
  b) marking the container with a human readable or 2-D matrix code which uniquely identifies individual containers without reducing visibility of the surface or the contents of the container;
  c) the code is applied using laser marker, ink-jet printer, or indelible print on an adhesive label applied to the surface of the container;
  d) each container is identified using an optical reading device such as machine vision system or bar code scanning device prior to placement in the inspection station;
  e) movement of particles in the container whereby rotation of the container using a predefined velocity motion profile causes substantially all of the particles in the solution in the container to experience a change in position with a corresponding change in time;

f) an image processing computer for image acquisition, image storage and image processing capability;

g) the image processing computer comprising memory for storing the images formed by the sensor;

h) the image processing computer also comprising digital parallel input/output digital serial, and Ethernet communication capabilities for providing messages to external devices to report one or more measurements or characteristics of the particles or area of different matter opacity;

i) the image processing computer executing control software stored in a computer-readable medium, which allows request and response signals from external devices indicating a specific size container to be inspected, which causes the image processing computer to perform image alignment and analysis for extraction of key characteristics in defined inspection zones in the container, as well as causing the image processing computer to store a reference images of an acceptable quality container in a memory location referenced by a specific identification code that is unique to a specific product or type, as well as causing a determination of the exact position of the container by extracting one or more edges of the reference container;

j) the image processing computer comprising memory for storing (recording) the properties of particles isolated in each defined inspection volume by each of the sensors;

k) recording the percentage of material with an opacity greater than a specified level isolated in each defined inspection volume by each of the sensors;

l) determine the mean of the particle properties in each defined inspection volume over "n" images, primary properties included the geometric shape and integration of grayscale values over the geometric shape using each of the sensors;

m) evaluate the particle only if its properties lie within a specific range of the mean of "x" samples and establish a mean equivalent pixel width in each corresponding inspection volume using each of the sensors;

n) creating a calibration curve by evaluating NIST traceable dimensional standards in a typical final container with a fill volume of WFI (water for injection) equivalent to that used for the product to the equivalent pixel width of the particle in each corresponding inspection volume for each of the sensors implementing in the system;

o) using one or more numerical calculations are performed to correlate particle size in pixels to equivalent physical dimension in micrometers using calibration curve established by measuring NIST traceable single seeded particle standards in each of the defined inspection volumes for each of the sensors implemented in the system;

p) characterized in that the one or more photo detector(s) are positioned relative to the container, whereby a focal point of detection coincides with the center of the cross sectional diameter, whereby the center of at least on of the detectors is positioned above the bottom of the container so to view substantially all of the container bottom, whereby the detected particles in solution move in the corresponding inspection volumes of the container; wherein said lighting means provides a contrasting geometric or grayscale size and shape of said particles as well as very sufficient grayscale sensitivity to detect solution opacity changes at least an order of magnitude better than human inspection techniques;

q) creating and storing a unique record for all of the inspection parameters, time of an inspection, date of an inspection, compiled and individual sensor inspection results, including but not limited to the number of particles present, the size of particles in measurement volumes, the fluid opacity and any changes as compared to the last inspection record.

2. The method of claim 1, wherein the invention has the ability to separate contaminating particles of a higher density from those of a lesser density.

3. The method of claim 2, wherein the measurement of particles is confined to the defined inspection volumes can identify contaminating particles from biological material.

4. The method of claim 1, wherein the invention can perform simultaneous independent evaluations of multiple inspection volumes within the same container.

5. The method of claim 1, wherein the measurement of small agglomerations of protein based matter (low density material) can be identified.

6. The method of claim 5, wherein the measurement of large (heavy) particles can be separated from the less dense agglomerations.

7. The method of claim 1, wherein the measurement of light extinction by contaminates in solution that cause a change in opacity may be detected with high grayscale resolving sensors.

8. The method of claim 7, wherein a series of individual measurements of the same container over a period of time may be used for the detection of biological contamination in solutions.

9. The method of claim 8, wherein the invention is capable of reducing the incubation time required before a determination of product contamination can be made.

10. The method of claim 8, wherein the invention is capable of measuring the rate of change of the cross-sectional area of product contamination between tests of individual samples.

11. The method of claim 8, wherein may be used to determine the presence of microbial growth in media fill solutions.

12. The method of claim 11, wherein the evidence of microbial growth in media fill solutions or tissue cultures may be determine in period of less than 30 hours using a series of test spaced several hours apart.

* * * * *